(12) United States Patent
Smith

(10) Patent No.: US 6,731,213 B1
(45) Date of Patent: May 4, 2004

(54) METHOD AND APPARATUS FOR PROVIDING ORAL HEALTH DATA

(75) Inventor: Michael G. Smith, Tustin, CA (US)

(73) Assignee: Gateway, Inc., Poway, CA (US)

( * ) Notice: Subject to any disclaimer, the term of this patent is extended or adjusted under 35 U.S.C. 154(b) by 181 days.

(21) Appl. No.: 09/871,124

(22) Filed: May 31, 2001

(51) Int. Cl.[7] ............................................ G08B 23/00
(52) U.S. Cl. .................... 340/573.1; 340/539; 340/665; 340/669; 340/611; 15/167.1; 15/21.1; 433/202.1; 433/37
(58) Field of Search ............................ 340/573.1, 611, 340/614, 619, 626, 665, 669, 539; 15/21.1, 22.1, 105.52, 167.1, 23, 24, 106; 433/202.1, 201.1, 26, 37; 128/903, 904; 600/300, 301

(56) References Cited

U.S. PATENT DOCUMENTS

| | | | |
|---|---|---|---|
| 5,438,726 A | 8/1995 | Leite | 15/105 |
| 5,561,881 A | * 10/1996 | Klinger et al. | 15/22.1 |
| 5,704,087 A | 1/1998 | Strub | 15/105 |
| 5,784,742 A | * 7/1998 | Giuliani et al. | 15/22.1 |
| 5,876,207 A | 3/1999 | Sundius et al. | 433/216 |
| 6,029,303 A | 2/2000 | Dewan | 15/105 |
| 6,081,957 A | 7/2000 | Webb | 15/105 |
| 6,093,019 A | * 7/2000 | Morandi et al. | 433/29 |
| 6,327,734 B1 | * 12/2001 | Meginniss, III et al. | 15/705 |
| 6,482,158 B2 | * 11/2002 | Mault | 600/437 |
| 2002/0133308 A1 | * 9/2002 | Lundell | 702/122 |

OTHER PUBLICATIONS

Instrument for measuring toothbrushing force using PIC microcontroller technology; www.nerac.com; Nov. 13, 2000.

Development of a force–sensing toothbrush instrument using PIC micro–controller technology for dental hygiene; Nov. 13, 2000.

* cited by examiner

Primary Examiner—Jeffery Hofsass
Assistant Examiner—Daniel Previl
(74) Attorney, Agent, or Firm—Scott Charles Richardson; Chad W. Swantz; Suiter - West

(57) ABSTRACT

The present invention is directed to an apparatus, system and method for detecting a user's oral health habits and providing the oral health data over a network for access by a remote user. For example, the user may utilize an oral health apparatus to brush his teeth. During brushing, oral health data may be obtained relating to the user's oral health habits and usage of the oral health apparatus. The oral health data may then be provided over a network to a remote user, such as the user's dental health professional or parent in the case of a young child.

35 Claims, 8 Drawing Sheets

METHOD AND APPARATUS FOR PROVIDING ORAL HEALTH DATA

FIELD OF THE INVENTION

The present invention generally relates to the field of health care data, and particularly to a method and apparatus for providing oral health data over a network for access by a remote user.

BACKGROUND OF THE INVENTION

In the past, oral health devices were operated independently. Thus, information concerning a user's habits would go uncollected. As a result, invaluable data about a user's oral health habits may go unnoticed. Due to this lack of information, a user's bad oral health habits typically would go unobserved until serious dilatory affects could be observed by a dental health professional.

Upon discovering oral health damage, a dental health professional is limited to recommending changes in oral health habits to avert similar damage in the future. Additionally, the dental health professional is limited to observing the results of the improper oral health habits at scheduled intervals without knowing even basic information about the patient's oral health habits. Without data about the patient's use of oral health devices, the dental health professional is limited to questioning the patient concerning the patient's oral health habits.

Previously, oral health devices were independent devices capable of sensing dental information. One drawback of previous oral health devices is the lack of communication of the gathered data. For example, although a device might be capable of detecting data regarding a user's brushing habits, such devices fail to communicate the data to a remote user, such as a dental health professional or a child's parent, for analysis.

For the foregoing reasons, there is a need for a device capable of sensing data regarding the user's oral health habits and communicating this data over a network for access by a remote user.

SUMMARY OF THE INVENTION

Accordingly, the present invention is directed to an apparatus, system and method for detecting a user's oral health habits and providing the oral health data over a network for access by a remote user. For example, the user may utilize an oral health apparatus to brush his teeth. During brushing, the apparatus may have a certain pressure applied to the user's teeth, achieve certain acceleration characteristics, and the like. As a result, oral health data may be obtained relating to the user's oral health habits and usage of the oral health apparatus. The oral health data may then be provided over a network to a remote user, such as the user's dental health professional or parent in the case of a young child. Consequently, the remote user may gain invaluable insight into the daily brushing habits of the user. Thus, the present invention overcomes the problems experienced with independent oral health devices.

In accordance with a first aspect of the present invention, an oral health apparatus includes at least one sensor suitable for detecting usage of the oral health apparatus by a user. The oral health apparatus also includes a communication device which is coupled to the sensor and is capable of providing the detected oral health data over a network for access by a remote user.

In a second aspect of the present invention, a networked oral health system includes a network suitable for communicating data, an oral health apparatus coupled to the network, and a remote information handling system coupled to the network. The oral health apparatus is capable of detecting oral health data about usage of the oral health apparatus by a user and communicating the detected oral health data over the network. The remote information handling system is then capable of accessing the detected oral health data over the network.

In a third aspect of the present invention, a method of providing data about usage of an oral health apparatus to a remote user includes detecting oral health data about usage of the oral health apparatus by a user and providing the detected oral health data over a network to a remote user.

In a further aspect of the present invention, a wireless communication link is provided between the oral health apparatus and the network, and thus, the monitoring of the user's oral health habits is accomplished as unobtrusively as possible.

It is to be understood that both the foregoing general description and the following detailed description are exemplary and explanatory only and are not restrictive of the invention claimed. The accompanying drawings, which are incorporated in and constitute a part of the specification, illustrate an embodiment of the invention and together with the general description, serve to explain the principles of the invention.

BRIEF DESCRIPTION OF THE DRAWINGS

The numerous advantages of the present invention may be better understood by those skilled in the art by reference to the accompanying figures in which.

DETAILED DESCRIPTION OF THE INVENTION

Reference will now be made in detail to the presently preferred embodiments of the invention, examples of which are illustrated in the accompanying drawings.

Figure 1:
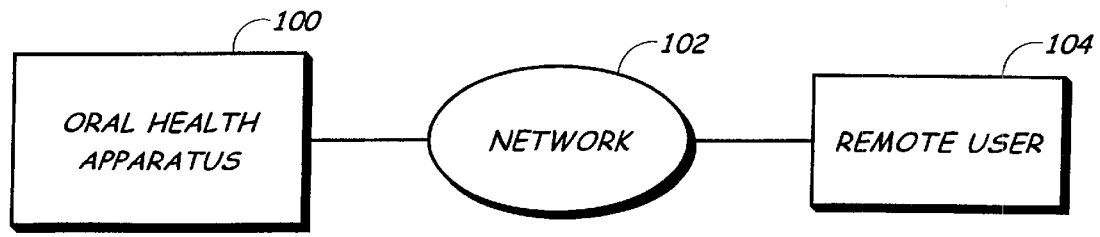
FIG. 1 is an illustration of an exemplary embodiment of the present invention accessible by a remote user.

Referring now to FIG. 1, an exemplary networked oral health apparatus 100 in accordance with the present invention is shown. The oral health apparatus 100 is suitable for providing oral health data over a network 102 to a remote user 104. Utilizing the present invention, invaluable insight into the user's oral health habits may be obtained by the remote user 104, such as the user's dental health professional, and in the case of a young child, the child's parent. For example, if the user fails to apply sufficient pressure while brushing his teeth, the apparatus 100 allows for observation by the user's dental health professional 104. In this way, the dental health professional 104 may access detailed records of the user's oral health habits and utilization of the oral health apparatus 100. Thus, the present invention may overcome problems encountered by independent oral health care devices.

Figure 2:
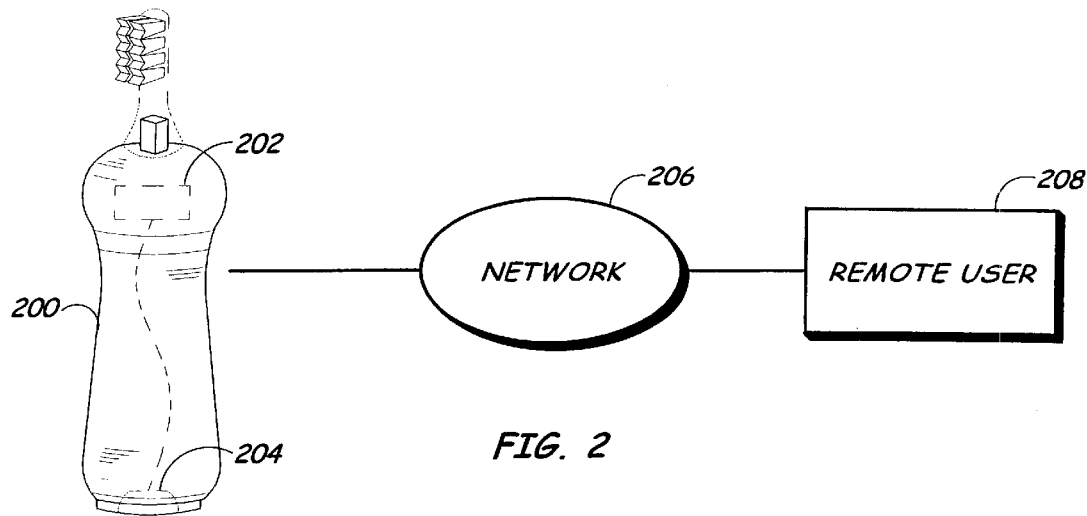
FIG. 2 is an illustration of an exemplary embodiment of the present invention with detecting and communicative ability.

Referring now to FIG. 2, an exemplary networked oral health apparatus 200 in accordance with the present invention is shown. The user of the oral health apparatus 200 may utilize the apparatus 200 to perform a desired oral health task. For example, a user may employ the apparatus 200 to brush his teeth. During use, a sensor 202 may detect the user's oral health habits. For example, the sensor 202 may be a timer for measuring the duration of use, a pressure gauge capable of detecting pressure applied by the user to the user's teeth, an accelerometer for measuring acceleration or vibrations of the oral health apparatus 200, a stress-strain meter capable of determining stress applied by the user to the oral health apparatus 200 and resulting strain on the oral health apparatus 200, a power sensing device for measuring the amount of power consumption by the oral health apparatus 200, a position sensing device capable of detecting position(s) of the oral health apparatus 200 within the user's mouth, an inclinometer for measuring the inclination of the oral health apparatus 200 relative to a horizontal axis (such as the user's teeth, tongue, lips, mouth, etc.), an oral contaminant sensing device for indicating the amount of oral contaminants in the user's mouth and the user's freshness of breath, and the like. It should be apparent that a wide variety of sensors 202 may be employed by the present invention as contemplated by a person of ordinary skill in the art and not depart from the spirit and scope of the present invention.

The sensor 202 is coupled to a communication device 204 suitable for communicating the oral health habits as oral health data. The communication device 204 is linked to a network 206 suitable for transferring the oral health data and enabling a remote user 208 to access the oral health data. Suitable networks 206 may include a local area network (LAN), a wide area network (WAN), a public switched telephone network (PSTN), the Internet, and the like. For example, the oral health apparatus 200 may include a pressure gauge and/or a position sensing device sensor 202 which detect the user's oral health habits. Upon observing the oral health data, the remote user 208 (e.g., a dental health professional) may determine that the user fails to apply sufficient pressure while brushing the sides of his teeth. From the present embodiment, it should be apparent to one of ordinary skill in the art that many combinations of wired and/or wireless links between the communication device 204 and the network 206 may be utilized, and it is the intent of the present invention to encompass such links without departing from the scope and spirit of the present invention.

Figure 3:
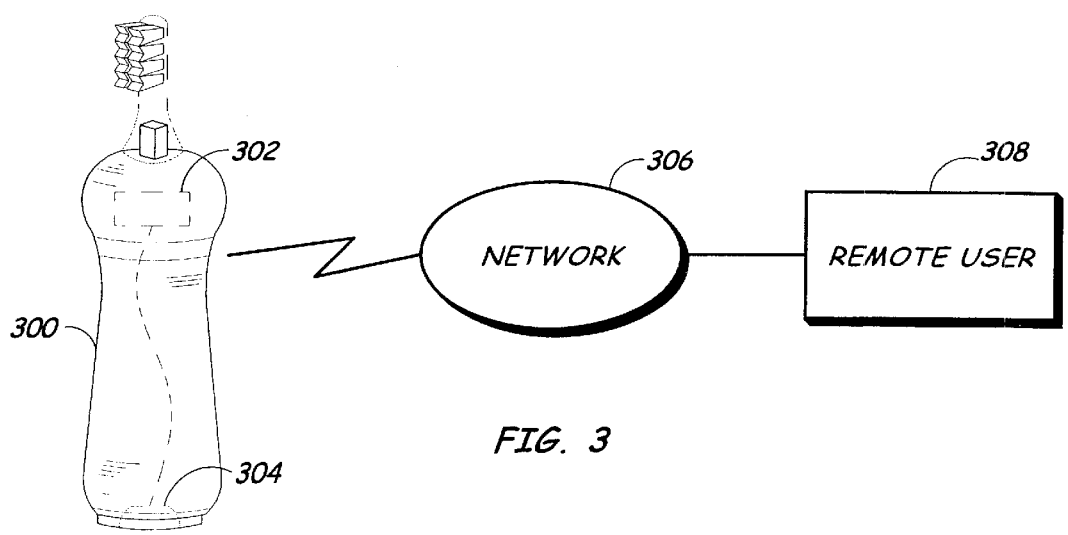
FIG. 3 is an exemplary networked oral health apparatus with wireless communicative ability.

Referring now to FIG. 3, in accordance with an embodiment of the present invention, an oral health apparatus 300 includes a communication device 304 coupled to a sensor 302. The oral health apparatus 300 utilizes the communication device 304 to communicate oral health data over a network 306 to a remote user 308. In this case, oral health habits are detected by the sensor 302 as oral health data. The oral health data may be transferred from the communication device 304 to the network 306, and then may be transmitted over the network 306 to the remote user 308. In the present embodiment, the communication device 304 communicates via wireless technology with the network 306. Suitable wireless technologies for the communication device 304 include Bluetooth, infrared, radio frequency, optical communication, and the like. Suitable networks 306 include a LAN, WAN, PSTN, the Internet, and the like. For example, the communication device 304 may be coupled to a pressure sensor 302, and may communicate via infrared technology with a LAN 306. As a result of the present arrangement, oral health data containing pressure information is received from the pressure sensor 302, and the communication device 304 is capable of transmitting the received oral health data via infrared technology to the LAN 306 for access by the remote user 308 over the LAN 306.

Figure 4A:
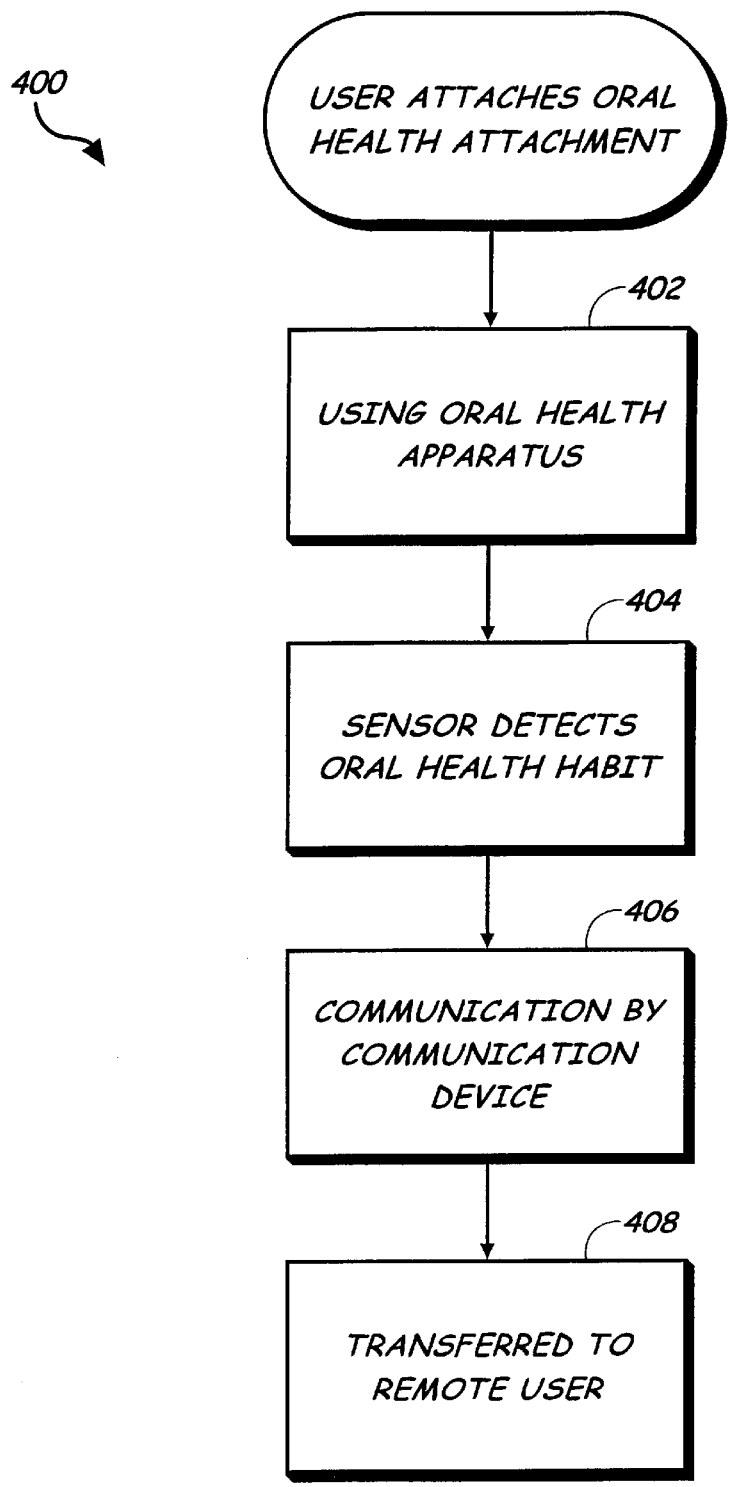
FIG. 4 is a flow diagram depicting an exemplary method of accessing oral health data over a network.

Referring now to FIG. 4A, a flow diagram depicting an exemplary method 400 of accessing oral health data over a network is shown. In step 402, a user employs an oral health apparatus to perform a desired oral health task, such as brushing his teeth. During brushing, the oral health apparatus may be manipulated in ways corresponding to the user's oral health habits. The oral health apparatus includes a sensor coupled to a communication device. In step 404, the sensor detects the user's oral health habits as oral health data, and in step 406, the communication device communicates the oral health data to a network. In step 408, the oral health data is then transferred over the network for access by a remote user. Networks suitable for transferring the oral health data may include a LAN, WAN, PSTN, the Internet, and the like. The oral health data may be transferred directly to the remote user, or alternatively, the oral health data may be transferred to a web site and the remote user may access the web site for the oral health data.

Figure 4B:
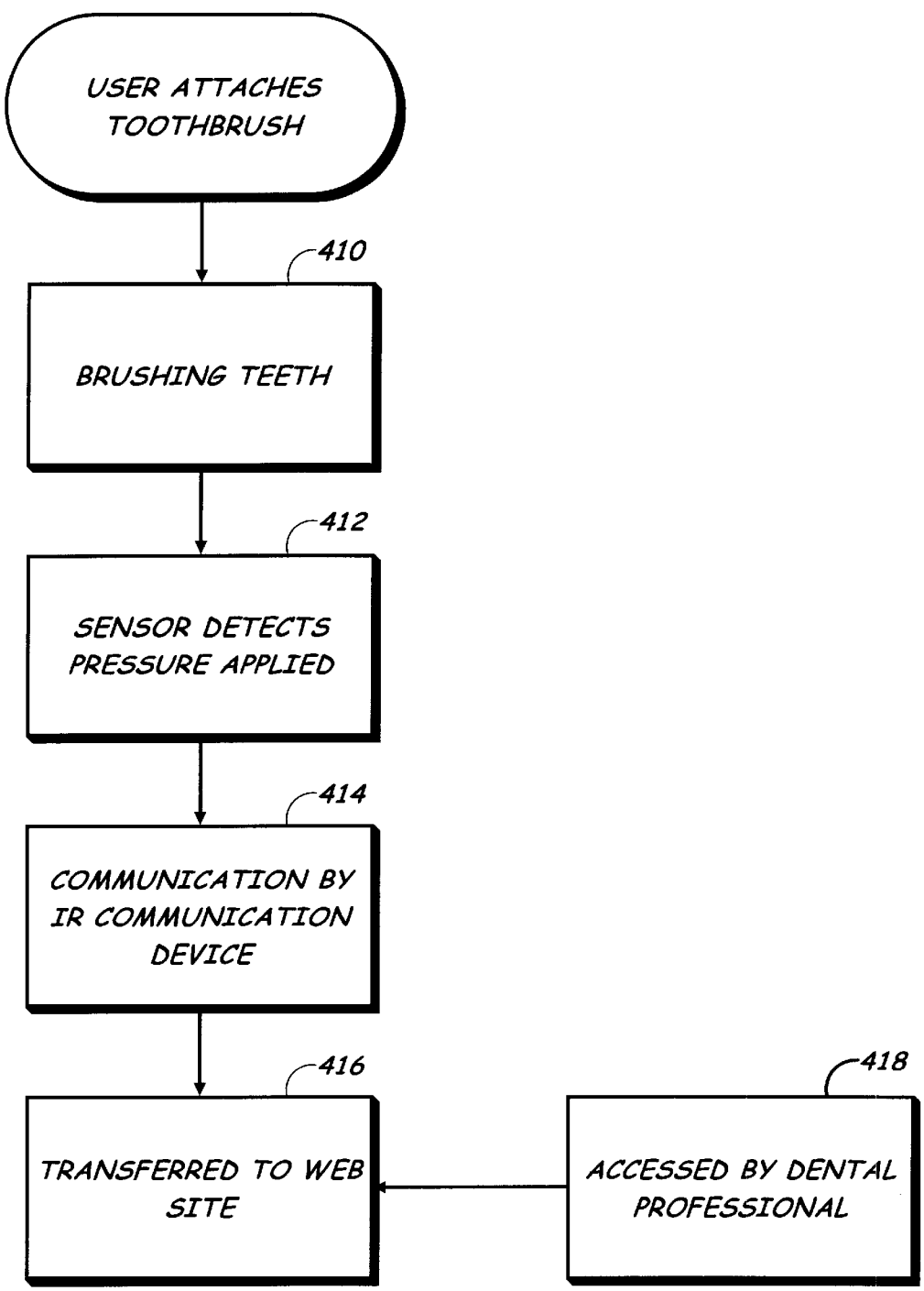

Referring now to FIG. 4B, a flow diagram depicting a method of accessing oral health data over a network is shown. In the present embodiment, a user employs an oral health apparatus, such as a toothbrush, to perform a desired oral health task, such as brushing the user's teeth, in step 410. During brushing, the oral health apparatus may be manipulated in ways corresponding to the user's oral health habits. In the present example, an oral health habit may consist of a certain pressure applied by the user while brushing. In step 412, the sensor detects the oral health habit (e.g., the pressure applied during brushing) and generates oral health data corresponding to the detected pressure. In step 414, the communication device communicates the oral health data via infrared technology to a network suitable for transferring the oral health data for access by a remote user, such as the Internet. In step 416, the oral health data is transferred over the Internet to a web site, and in step 418, the oral health data is accessed through the web site by the user's dental health care professional prior and/or during the user's scheduled checkup.

Figure 5:
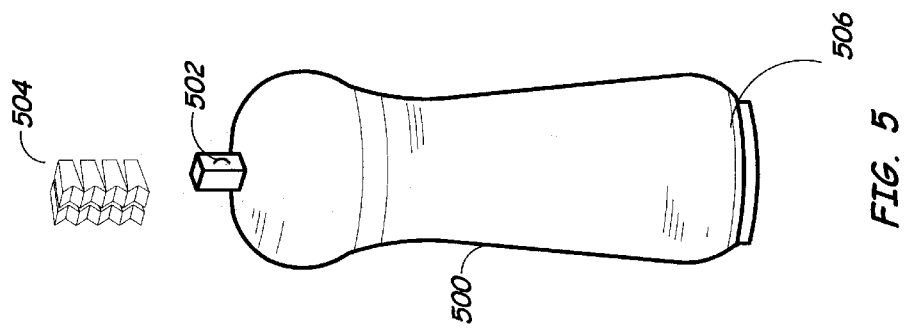
FIG. 5 is an illustration of an exemplary embodiment of the present invention showing a user identification device suitable for detecting the user's identity based on an electrical connection.

Referring now to FIG. 5, an oral health apparatus 500 employing the present invention may be used to interact with an oral health attachment 504. The oral health attachment 504 may include a toothbrush, a dental floss holder, a tongue scraper, and the like. For example, the oral health apparatus 500 may be designed to connect to a removable toothbrush 504. The oral health apparatus 500 also includes a user identification device 502, such as a sensor 502, which is coupled to a communication device 506 and is suitable for identifying the user based on an identifiable characteristic, such as the oral health attachment 504 selected by the user, and the like. For example, the user of the oral health apparatus 500 may be determined based on his selection of oral health attachment 504 through the use of: an identification chip, a mechanical connection, an electrical connection, an identifiable characteristic of the oral health attachment 504, and the like. Examples of identifiable characteristics of the oral health attachment 504 include color, shape, pattern, and the like. For example, selecting a blue toothbrush 504 may identify a user. The blue toothbrush 504 may include a computer chip suitable for identification by the user identification device 502.

Figure 6:
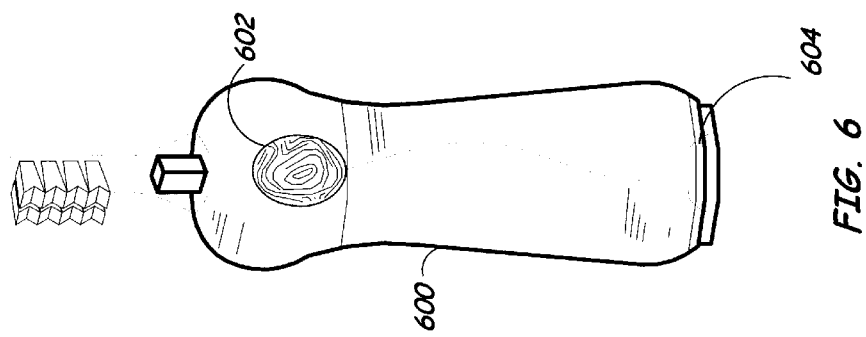
FIG. 6 is an illustration of an exemplary embodiment of the present invention showing a user identification device suitable for detecting the user's identity based on a fingerprint.

Referring to FIG. 6, an oral health apparatus 600 may include a user identification device 602, which is coupled to a communication device 604 and is suitable for identifying a user based on an identifiable characteristic, such as a feature associable with the user. For example, a fingerprint scanner 602 may be used to identify the user of the oral health apparatus 600 by a designated fingerprint, such as the user's right thumbprint. Other identifiable characteristics include an oral characteristic, such as the user's teeth, and the like.

Figure 7:
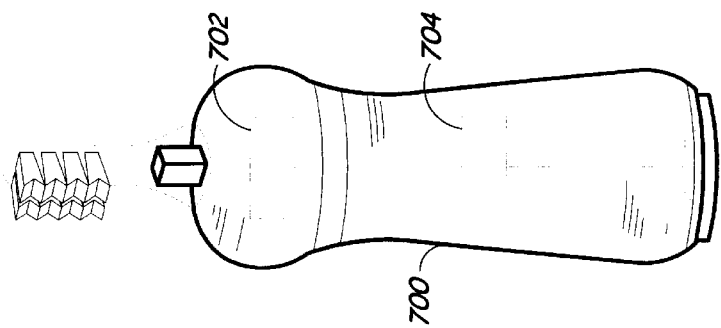
FIG. 7 is an illustration of an exemplary embodiment of the present invention wherein a memory device is coupled to a sensor.

FIG. 7 shows a presently preferred embodiment of an oral health apparatus 700 including at least one sensor 702 and a memory device 704. The memory device 704 is coupled to the sensor 702 and stores oral health data detected by the sensor 702. The memory device 704 may be a removable memory device, such as a memory stick, memory card, microdrive, and the like. Alternatively, the memory device 704 may be a non-removable memory device, such as a hard disk drive. It is to be understood that the memory device 704 may be disposed at various locations on the oral health apparatus 700, as contemplated by one of ordinary skill in the art without departing from the spirit and scope of the present invention.

Figure 8:
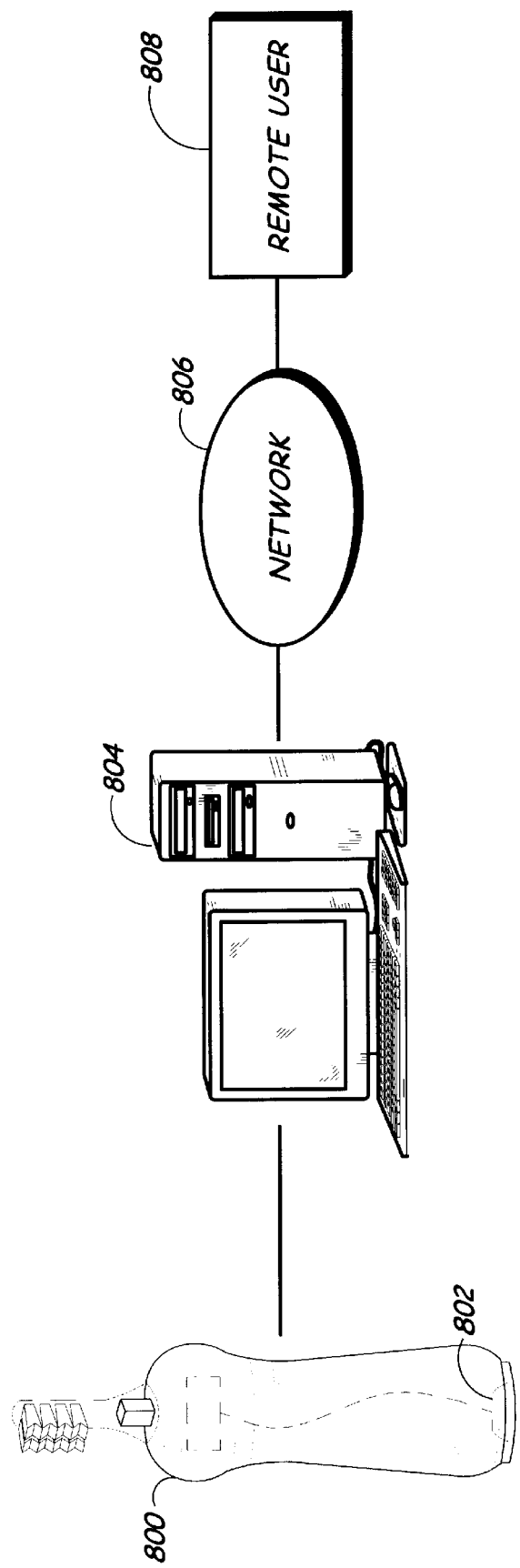
FIG. 8 is an illustration of an exemplary embodiment of the present invention wherein an information handling system links an oral health apparatus to a network.

In a further embodiment shown in FIG. 8, a networked oral health apparatus 800 is communicatively linked to a local information handling system 804. In this embodiment, the local information handling system 804 forms the interface between a communication device 802 in the apparatus 800 and a network 806. The communication device 802 provides the oral health data to the local information handling system 804, which then transfers the oral health data to the network 806. The local information handling system 804 may be a standalone system, which is coupled to the network 806. Alternatively, the local information handling system 804 may also belong to the network 806, such as a LAN or WAN. Further, the local information handling system 804 may belong to another network distinct from, but coupled to, the network 806 (e.g., the local information handling system 804 may belong to a LAN, which is then coupled to the network 806, such as the Internet).

Inclusion of the local information handling system 804 allows the user to access the oral health data either directly from the oral health apparatus 800, or in the same fashion as a remote user 808, for example, by accessing a web site storing the oral health data. In the presently preferred embodiment, the local information handling system 804 may be configured to store the oral health data. For instance, the oral health data may be stored on the local information handling system 804 and then accessed through the network 806 during the user's dental checkup.

Figure 9:
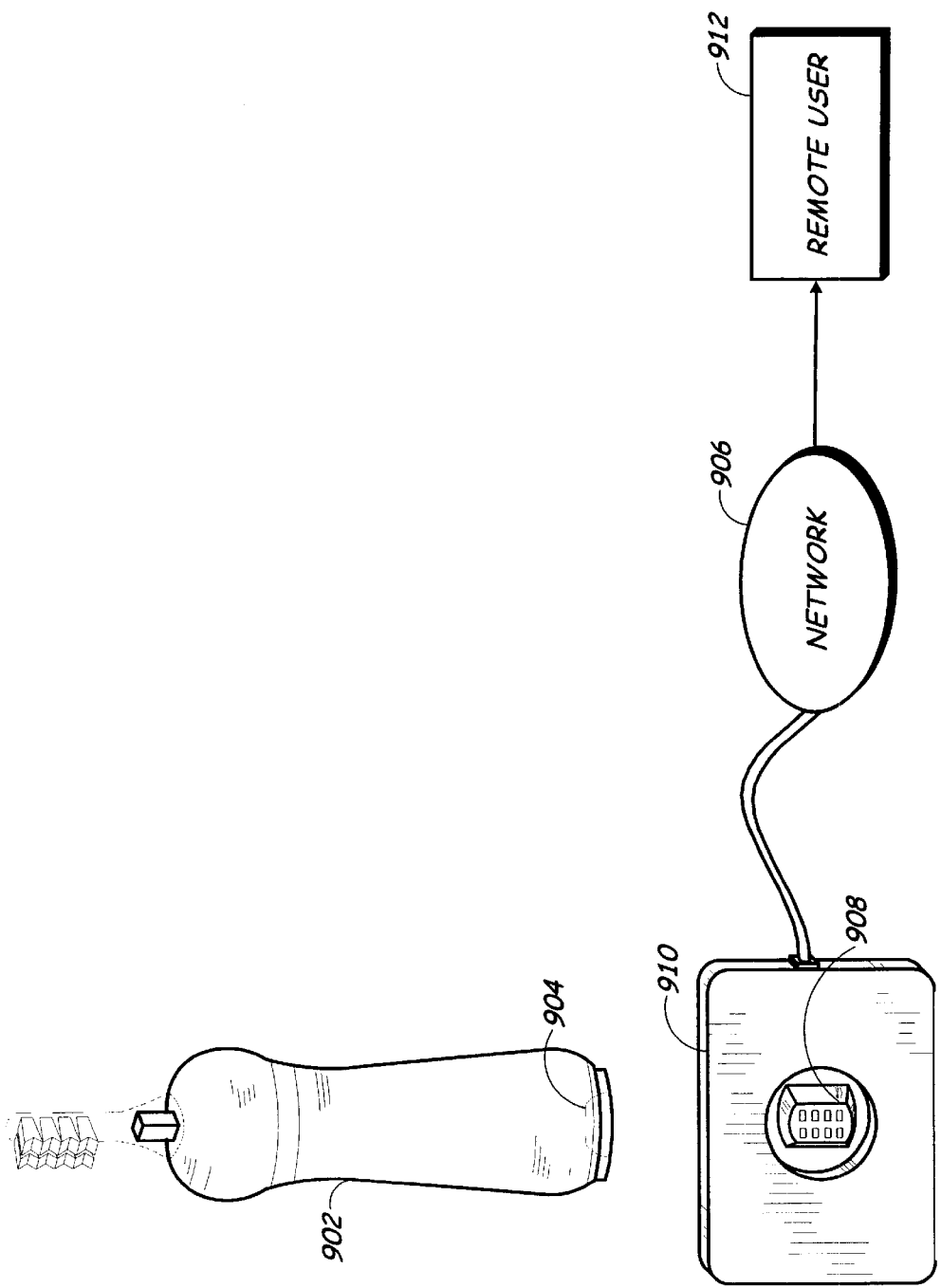
FIG. 9 is an illustration of an exemplary embodiment of the present invention wherein a communication device is suitable for connecting to a port.

Referring to FIG. 9, an exemplary embodiment of an oral health apparatus 902 including a communication device 904 suitable for linking to a network 906 via a port 908 is shown. The communication device 904 may be mechanically attached to and detached from the port 908. During use (e.g., while the user brushes his teeth), the oral health apparatus 902 is not connected to the port 908. When the user has completed the oral health task, he may reconnect the oral health apparatus 902 to the port 908, and thus, connect the communication device 904 to the port 908 to allow for the transfer of oral health data.

The oral health apparatus 902 may be additionally suited for use where wireless communication is impractical. For example, the user may choose to take the oral health apparatus 902 while camping. The oral health apparatus 902 having the communication device 904 enables the user to collect oral health data while away from the user's normal environment and download the data upon his return. Ports 908 suitable for communicating the oral health data from the oral health apparatus 902 to the network 906 include a USB port, an IEEE 1394 port, and the like. The port 908 may be disposed on a stand 910 as a direct connection to an information handling system and the like, as contemplated by one of ordinary skill in the art.

Figure 10:
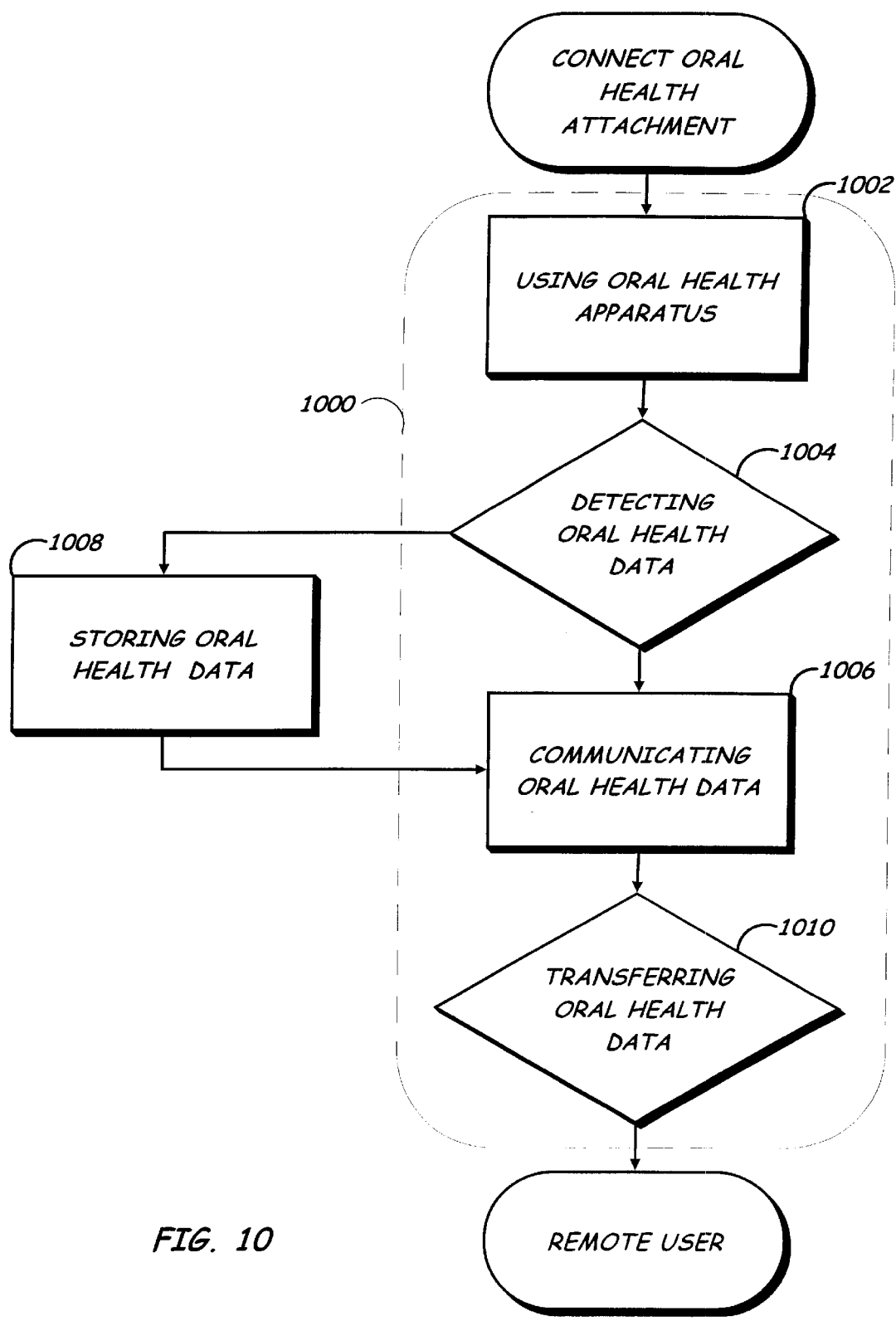
FIG. 10 is a flow diagram of the present invention showing an exemplary method of providing oral health data to a remote user.

Referring now to FIG. 10, an exemplary method 1000 of providing oral health data to a remote user, such as a user's dental health professional, a user's parent if the user is a child, and the like, is presented. In the present embodiment, an oral health apparatus is used to perform the desired oral health task, such as brushing the user's teeth, in step 1002. The oral health apparatus may be utilized to perform a wide variety of oral health tasks without departing from the spirit and scope of the present invention. During use, the user manipulates the oral health apparatus to accomplish the desired oral health task. As a result, the apparatus may be manipulated in certain ways corresponding to the user's oral health habits. For example, the user may apply a certain amount of pressure to a toothbrush attachment.

In step 1004, one or more sensors on the oral health apparatus may detect the user's oral health habits, and oral health data corresponding to the user's habits is generated. The oral health data may include the duration of usage of the oral health apparatus, pressure applied by the user to his teeth, acceleration or vibration of the oral health apparatus, stress applied by the user to the oral health apparatus and/or resulting strain on the oral health apparatus, amount of power consumption by the oral health apparatus, position(s) of the oral health apparatus within the user's mouth, inclination of the oral health apparatus relative to a horizontal axis such as the user's tongue, amount of oral contaminants in the user's mouth, and the like. For example, a pressure gauge may detect large variations in the amount of pressure applied by the user to his teeth.

In step 1006, a communication device coupled to the sensor communicates the oral health data to a network. The communication device may connect to the network through a port, wireless link, and the like. For example, the oral health data may be communicated to the network through the use of a communication device operating in compliance with the Bluetooth standard. Alternatively, as shown in FIG. 10, a memory device may be coupled to the sensor, and the oral health data may be stored on the memory device in step 1008 prior to communicating the oral health data to the network in step 1006. In the present embodiment, the oral health data is then transferred over the network to a remote user in step 1010.

Figure 11:
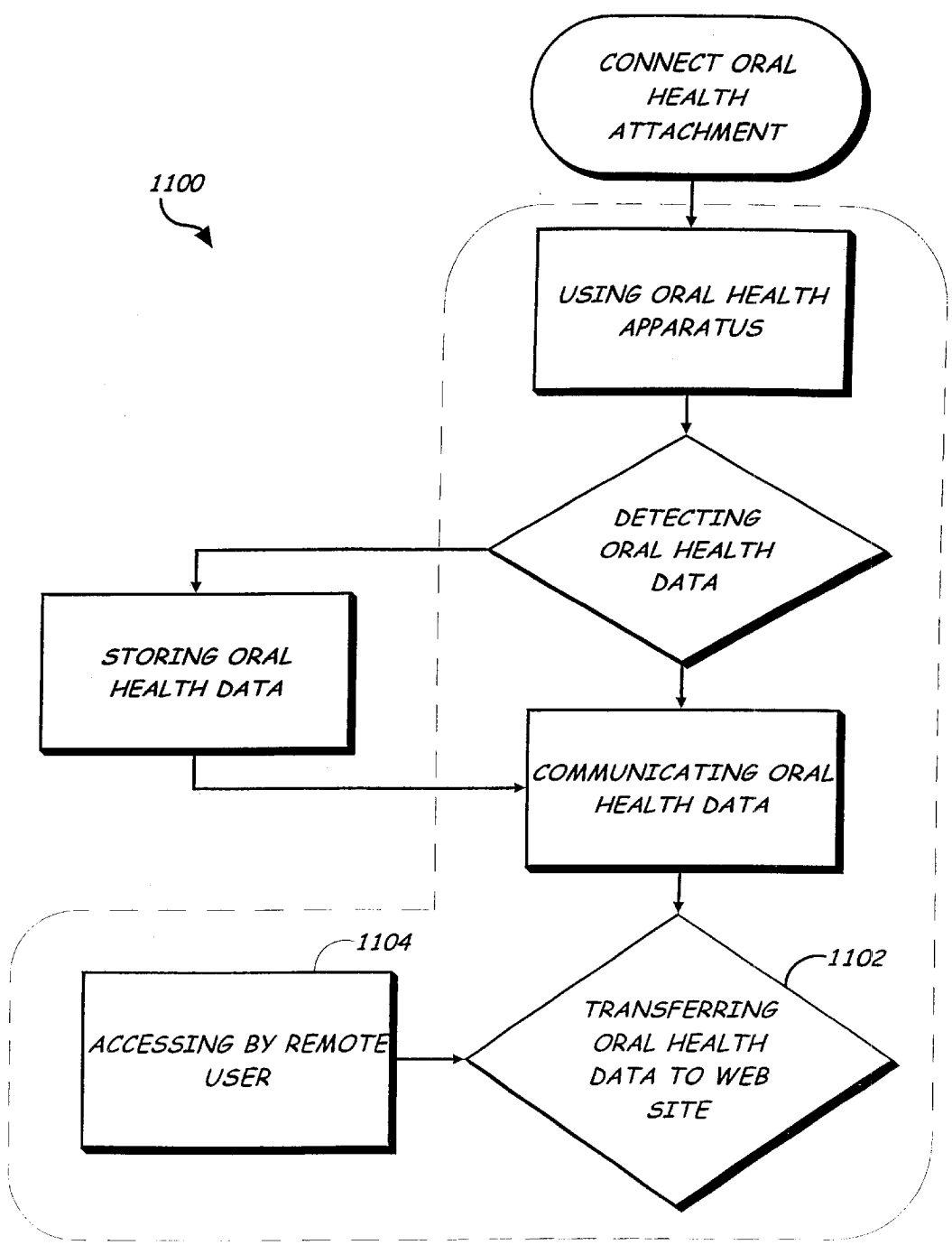
FIG. 11 is a flow diagram of the present invention showing an exemplary method of providing oral health data to a web site for access by a remote user.

Referring now to FIG. 11, an exemplary method 1100 of providing oral health data to a web site for access by a remote user, such as a user's dental health professional, a user's parent if the user is a child, and the like, is presented. In the present embodiment, steps 1002–1008 described above in reference to FIG. 10 are similarly performed. In the present method, after the oral health data is communicated to the network in step 1006, the oral health data is transferred to a web site in step 1102. Upon accessing the web site in step 1104, a remote user is able to transfer the oral health data to his information handling system, work with the data on the web site, and the like.

In exemplary embodiments, the methods disclosed may be implemented as sets of instructions or software readable by a device. Further, it is understood that the specific order or hierarchy of steps in the methods disclosed are exemplary approaches. Based upon design preferences, it is understood that the specific order or hierarchy of steps in the method can be rearranged while remaining within the scope of the present invention. The accompanying method claims present elements of the various steps in a sample order, and are not meant to be limited to the specific order or hierarchy presented.

It is believed that the method and apparatus for providing oral health data of the present invention and many of its attendant advantages will be understood by the foregoing description. It is also believed that it will be apparent that various changes may be made in the form, construction and arrangement of the components thereof without departing from the scope and spirit of the invention or without sacrificing all of its material advantages, the form herein before described being merely an explanatory embodiment thereof. It is the intention of the following claims to encompass and include such changes.

What is claimed is:

1. An oral health apparatus, comprising:
    a sensor, said sensor detecting oral health data about usage of the oral health apparatus by a user, said sensor including:
        a timer for measuring a duration of use of the apparatus;
        a pressure gauge for detecting pressure applied by said user to teeth of said user;
        a position sensing device for detecting at least one position of the oral health apparatus within a mouth of said user; and
        an oral contaminant sensing device for indicating an amount of oral contaminants within the mouth of said user; and
    a communication device coupled to the sensor, the communication device being capable of providing the detected oral health data to a network for access by a remote user.

2. The oral health apparatus as described in claim 1, wherein the sensor further includes an accelerometer, a stress-strain meter, a power sensing device, and an inclinometer.

3. The oral health apparatus as described in claim 1, wherein the detected oral health data includes acceleration of the oral health apparatus, stress applied by the user to the oral health apparatus, strain on the oral health apparatus resulting from the usage of the oral health apparatus, power consumption by the oral health apparatus and inclination of the oral health apparatus relative to a horizontal axis.

4. The oral health apparatus as described in claim 1, wherein the communication device is capable of providing the detected oral health data to the network via wireless technology.

5. The oral health apparatus as described in claim 4, wherein the wireless technology includes at least one of: infrared (IR), radio frequency (RF), Bluetooth, and optical.

6. The oral health apparatus as described in claim 1, wherein the network includes at least one of: a local area network (LAN), a wide area network (WAN), a public switched telephone network (PSTN), and the Internet.

7. The oral health apparatus as described in claim 1, further comprising a memory device coupled to the at least one sensor, the memory device being capable of storing the detected oral health data.

8. The oral health apparatus as described in claim 1, further comprising a user identification device coupled to the communication device, the user identification device being capable of identifying the user based on a characteristic of one of: the oral health apparatus and the user.

9. The oral health apparatus as described in claim 8, wherein the user identification device is capable of identifying the user based on a characteristic of the user, the characteristic of the user being one of: a fingerprint and an oral feature.

10. The oral health apparatus as described in claim 8, wherein the user identification device is capable of identifying the user based on a characteristic of the oral health apparatus, the characteristic of the oral health apparatus being one of: a color, a shape, and a pattern.

11. The oral health apparatus as described in claim 1, wherein the communication device is further capable of providing the detected oral health data to the network via a port, the port being capable of coupling the oral health apparatus to the network.

12. An oral health system, comprising:
    a network capable of communicating data;
    an oral health apparatus coupled to the network, the oral health apparatus including:
        sensor capable of detecting oral health data about usage of the
        oral health apparatus by a user, said sensor including:
            a timer for measuring a duration of use of the apparatus;
            a pressure gauge for detecting pressure applied by said user to teeth of said user;
            a position sensing device for detecting at least one position of the oral health apparatus within a mouth of said user; and
            an oral contaminant sensing device for indicating an amount of oral contaminants within the mouth of said user; and
        a communication device coupled to the sensor and the network, the communication device being capable of communicating the detected oral health data over the network; and
    a remote information handling system coupled to the network, the remote information handling system being capable of accessing the detected oral health data over the network.

13. The oral health system as described in claim 12, wherein the further includes an accelerometer, a stress-strain meter, a power sensing device, and an inclinometer.

14. The oral health system as described in claim 12, wherein the detected oral health data includes acceleration of the oral health apparatus, stress applied by the user to the oral health apparatus, strain on the oral health apparatus resulting from the usage of the oral health apparatus, power consumption by the oral health apparatus, and inclination of the oral health apparatus relative to a horizontal axis.

15. The oral health system as described in claim 12, wherein the network includes at least one of: a local area network (LAN), a wide area network (WAN), a public switched telephone network (PSTN), and the Internet.

16. The oral health system as described in claim 12, wherein the communication device is capable of providing the detected oral health data to the network via wireless technology.

17. The oral health system as described in claim 16, wherein the wireless technology includes at least one of: infrared (IR), radio frequency (RF), Bluetooth, and optical.

18. The oral health system as described in claim 12, further comprising a local information handling system coupled between the oral health apparatus and the network, the local information handling system being capable of accessing the detected oral health data.

19. The oral health system as described in claim 12, wherein the oral health apparatus further includes a memory device coupled to the at least one sensor, the memory device being capable of storing the detected oral health data.

20. The oral health system as described in claim 12, wherein the oral health apparatus further includes a user identification device coupled to the communication device, the user identification device being capable of identifying the user based on a characteristic of one of: the oral health apparatus and the user.

21. The oral health system as described in claim 12, further comprising a port capable of coupling the oral health apparatus to the network.

22. A method of providing data about usage of an oral health apparatus to a remote user, comprising:

detecting an oral health data about the usage of the oral health apparatus by a user, said oral health data including duration of the usage of the oral health apparatus, pressure applied by the user to the user's teeth, at least one position of the oral health apparatus within the user's mouth, and amount of oral contaminants in the user's mouth; and communicating the detected oral health data over a network for access by the remote user.

23. The method as described in claim 22, wherein the detected oral health data further includes acceleration of the oral health apparatus, stress applied by the user to the oral health apparatus, strain on the oral health apparatus resulting from the usage of the oral health apparatus, power consumption by the oral health apparatus, and inclination of the oral health apparatus relative to a horizontal axis.

24. The method as described in claim 22, wherein the communicating step further comprises the step of: communicating the detected oral health data to the network via wireless technology.

25. The method as described in claim 24, wherein the wireless technology includes at least one of: infrared (IR), radio frequency (RF), Bluetooth, and optical.

26. The method as described in claim 22, wherein the network includes at least one of: a local area network (LAN), a wide area network (WAN), a public switched telephone network (PSTN), and the Internet.

27. The method as described in claim 22, further comprising storing the oral health data.

28. The method as described in claim 22, further comprising identifying the user based on a characteristic of one of: the oral health apparatus and the user.

29. An oral health apparatus, comprising:

means for detecting an oral health data about usage of the oral health apparatus by a user, said oral health data including duration of the usage of the oral health apparatus, pressure applied by the user to the user's teeth, at least one position of the oral health apparatus within the user's mouth, and amount of oral contaminants in the user's mouth; and means for communicating the detected oral health data over a network for access by the remote user.

30. The oral health apparatus as described in claim 29, wherein the detected oral health data further includes acceleration of the oral health apparatus, stress applied by the user to the oral health apparatus, strain on the oral health apparatus resulting from the usage of the oral health apparatus, power consumption by the oral health apparatus, and inclination of the oral health apparatus relative to a horizontal axis.

31. The oral health apparatus as described in claim 29, further comprising means for communicating the detected oral health data to the network via wireless technology.

32. The oral health apparatus as described in claim 31, wherein the wireless technology includes at least one of: infrared (IR), radio frequency (RF), Bluetooth, and optical.

33. The oral health apparatus as described in claim 29, wherein the network includes at least one of: a local area network (LAN), a wide area network (WAN), a public switched telephone network (PSTN), and the Internet.

34. The oral health apparatus as described in claim 29, further comprising means for storing the oral health data.

35. The oral health apparatus as described in claim 29, further comprising means for identifying the user based on a characteristic of one of: the oral health apparatus and the user.

* * * * *